US008284893B2

(12) United States Patent
Noshi

(10) Patent No.: US 8,284,893 B2
(45) Date of Patent: Oct. 9, 2012

(54) X-RAY COMPUTER TOMOGRAPHY APPARATUS AND IMAGE PROCESSING APPARATUS

(75) Inventor: Yasuhiro Noshi, Otawara (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 452 days.

(21) Appl. No.: 12/560,197

(22) Filed: Sep. 15, 2009

(65) Prior Publication Data

US 2010/0080433 A1   Apr. 1, 2010

(30) Foreign Application Priority Data

Sep. 29, 2008   (JP) ................................. 2008-251682

(51) Int. Cl.
*A61B 6/03*        (2006.01)
(52) U.S. Cl. .......................................... 378/7; 382/131
(58) Field of Classification Search .................. 378/4, 7; 382/128–132
See application file for complete search history.

(56) References Cited

U.S. PATENT DOCUMENTS 5,014,293 A * 5/1991 Boyd et al. ..................... 378/197

FOREIGN PATENT DOCUMENTS

JP   2002-246583 A     8/2002
JP     2006125922 A *  5/2006

* cited by examiner

*Primary Examiner* — Toan Ton
*Assistant Examiner* — John Corbett
(74) *Attorney, Agent, or Firm* — Knoble Yoshida & Dunleavy, LLC

(57) ABSTRACT

An X-ray computer tomography apparatus includes an X-ray tube, an X-ray detector, a rotating mechanism, a reconstruction unit which reconstructs multislice or volume image data based on the projection data detected by the X-ray detector, a profile generating unit which generates a CT value profile in the slice direction for each pixel by using image data, a profile portion extraction unit which extracts a profile portion exceeding a predetermined threshold from each of the CT value profiles, a scattered radiation distribution estimation unit which estimates a scattered radiation distribution centered on the profile portion based on the CT value integral and width of the profile portion, and a scattered radiation correction unit which corrects the image data based on the estimated scattered radiation distribution.

10 Claims, 8 Drawing Sheets

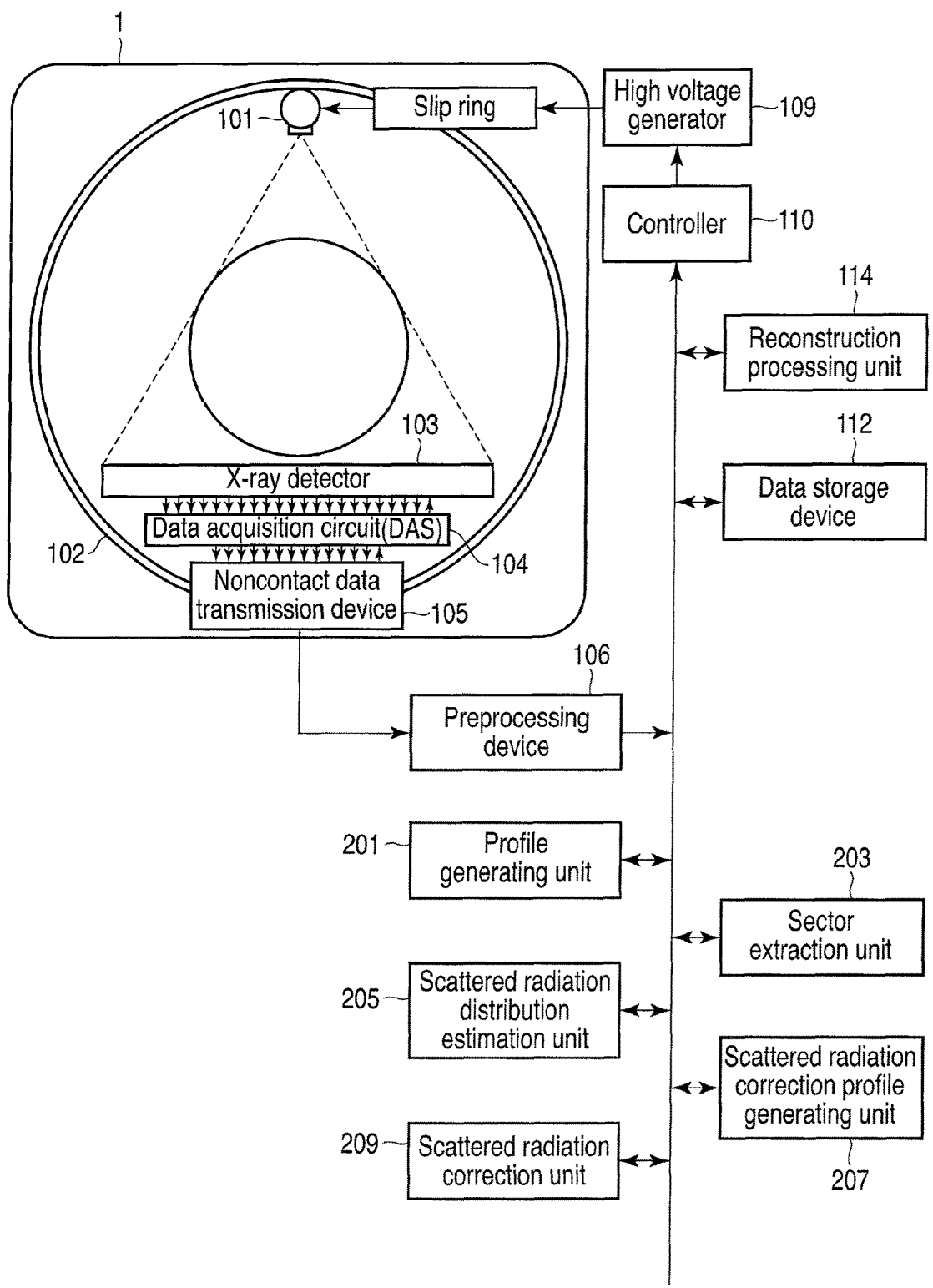
F I G. 1

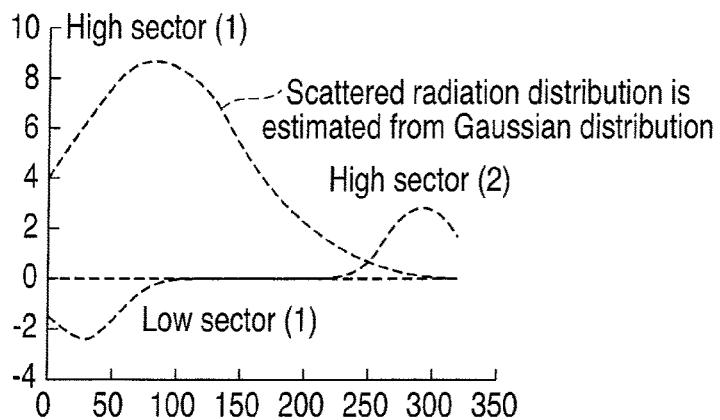
F I G. 5
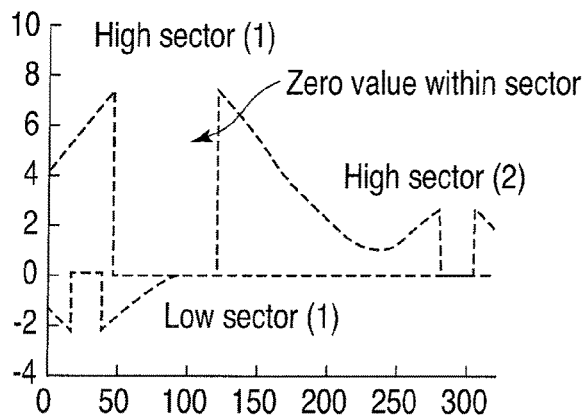
F I G. 6
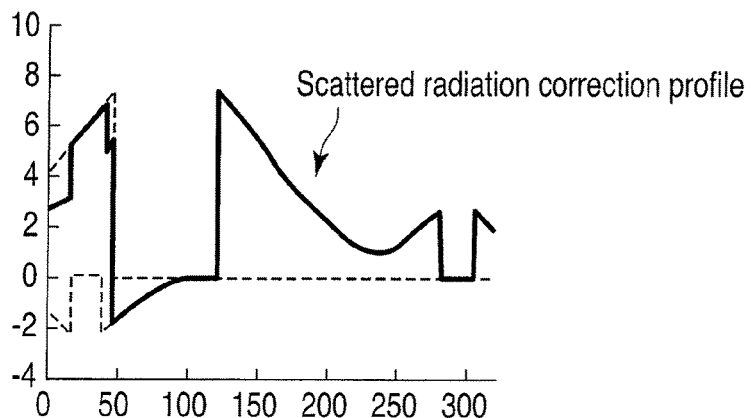
F I G. 7

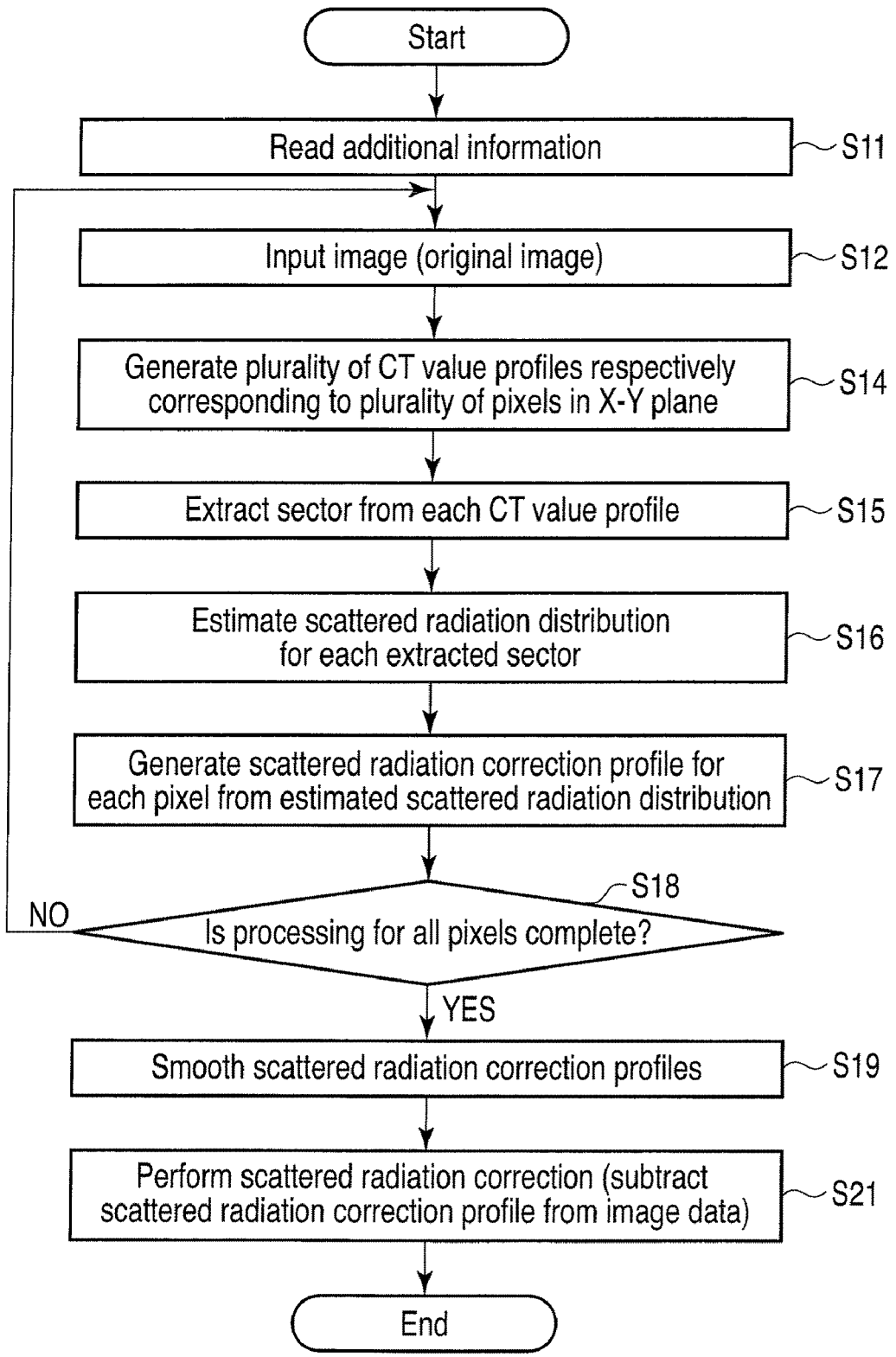
F I G. 9

US 8,284,893 B2

X-RAY COMPUTER TOMOGRAPHY APPARATUS AND IMAGE PROCESSING APPARATUS

CROSS-REFERENCE TO RELATED APPLICATIONS

This application is based upon and claims the benefit of priority from prior Japanese Patent Application No. 2008-251682, filed Sep. 29, 2008, the entire contents of which are incorporated herein by reference.

BACKGROUND OF THE INVENTION

1. Field of the Invention

The present invention relates to an X-ray computer tomography apparatus which can generate image data in a multislice or volume form and an image processing apparatus.

2. Description of the Related Art

An X-ray computer tomography apparatus provides information about an object by means of images based on the intensity of X-rays transmitted through the object. This apparatus plays an important role in many medical practices including diagnosis of diseases, medical treatments, and surgical plans.

In this X-ray computer tomography apparatus, with an increase in the number of detection element arrays of a detector, the influence of scattered radiation cannot be neglected. Therefore, there is available a technique of correcting scattered radiation components on projection data and reconstructing an image based on the projection data having undergone scattered radiation correction.

In correction on projection data (raw data), however, the amount of data to be processed is large, and hence it takes much time to perform correction. In addition, with an increase in the number of arrays, an increase in load on disk capacity for storing raw data cannot be neglected. Refer to Jpn. Pat. Appln. KOKAI Publication No. 2002-246583 for these conventional techniques.

BRIEF SUMMARY OF THE INVENTION

It is an object of the present invention to improve the processing efficiency of scattered radiation correction in a cone-beam X-ray computer tomography apparatus.

According to an aspect of the present invention, there is provided an X-ray computer tomography apparatus comprising:

an X-ray tube which generates X-rays;

an X-ray detector which detects X-rays transmitted through an object;

a rotating mechanism which continuously rotates the X-ray tube and the X-ray detector around the object;

a reconstruction unit which reconstructs one of multislice image data and volume image data based on projection data detected by the X-ray detector;

a profile generating unit which generates a plurality of CT value profiles in a slice direction which respectively correspond to a plurality of pixels in a slice by using the image data;

a profile portion extraction unit which extracts a profile portion exceeding a predetermined threshold from each of the CT value profiles;

a scattered radiation distribution estimation unit which estimates a scattered radiation distribution centered on the profile portion, based on a CT value integral and width of the profile portion; and a scattered radiation correction unit which corrects the image data based on the estimated scattered radiation distribution.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an X-ray computer tomography apparatus according to an embodiment of the present invention;

FIG. 5 is a graph showing an example of a scattered radiation distribution in the slice direction estimated by a scattered radiation distribution estimation unit in FIG. 1;

FIG. 6 is a graph for explaining weighting processing by a scattered radiation correction profile generating unit in FIG. 1;

FIG. 7 is a graph showing an example of a scattered radiation correction profile generated by the scattered radiation correction profile generating unit in FIG. 1;

FIG. 9 is a flowchart showing another scattered radiation correction processing procedure according to this embodiment;

DETAILED DESCRIPTION OF THE INVENTION

Figure 2:
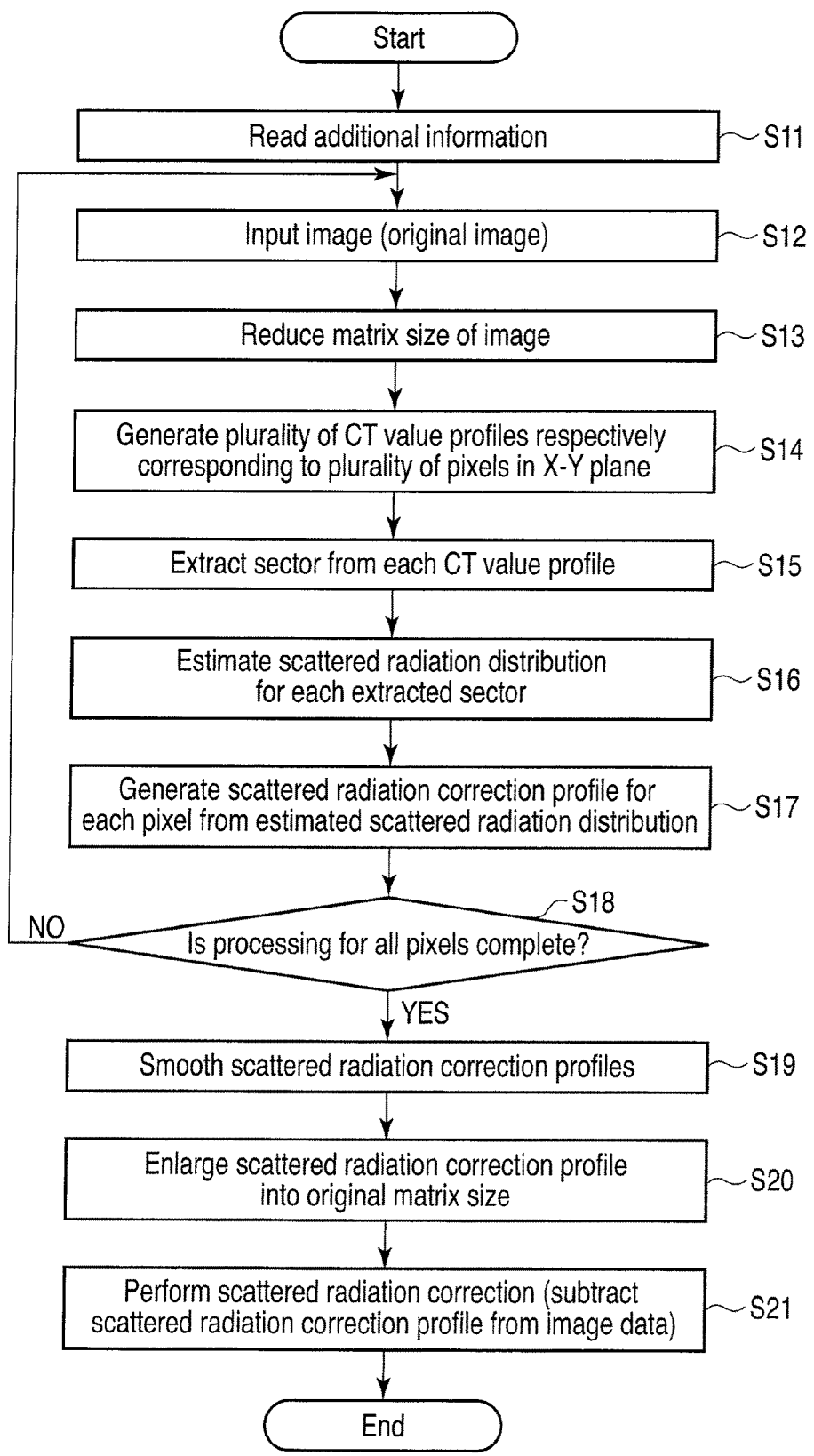
FIG. 2 is a flowchart showing a scattered radiation correction processing procedure in this embodiment.

An embodiment of an X-ray computer tomography apparatus including an image processing apparatus according to the present invention will be described below with reference to the views of the accompanying drawing. Note that X-ray computer tomography apparatuses include various types of apparatuses such as a rotate/rotate-type apparatus in which an X-ray tube and an X-ray detector rotate together around an object, and a stationary/rotate-type apparatus in which many detection elements are arrayed in the form of a ring, and only an X-ray tube rotates around an object. The present invention can be applied to either type. This apparatus will be described as the rotate/rotate type which is currently mainstream. Mainstream mechanisms for converting incident X-rays into electric charges are an indirect conversion type that converts X-rays into light through a phosphor such as a scintillator and further converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. Either type can be used as an X-ray detection element. In this case, the former indirect conversion type will be exemplified. In addition, a so-called multi-tube X-ray computer tomography apparatus having a plurality of pairs of X-ray tubes and X-ray detectors on a rotating ring has been commercially available in recent years, and peripheral techniques have been developed accordingly. The present invention can be applied to either a conventional single-tube X-ray computer tomography apparatus or a multi-tube X-ray computer tomography apparatus. In this case, the single-tube type will be exemplified.

FIG. 1 shows the arrangement of an X-ray computer tomography apparatus according to this embodiment. The X-ray computer tomography apparatus includes a gantry 1 configured to acquire projection data concerning an object. The gantry 1 includes an X-ray tube 101 and an X-ray detector 103. As the X-ray detector 103, for example, a 64-array multislice type (multi-array type) detector covering a cardiac region is typically used.

The X-ray tube 101 and the X-ray detector 103 are mounted on a ring-like rotating frame 102 which is rotated/driven. In this case, the rotation axis of the rotating frame 102 is defined as a Z-axis. In a rotating coordinate system centered on the Z-axis, an axis which connects the focus of the X-ray tube 101 and the detection surface center of the X-ray detector 103 and is perpendicular to the Z-axis is defined as an X-axis. The Y-axis is perpendicular to both the Z-axis and the X-axis. An opening portion is formed in both the central portion of the rotating frame 102 and the housing. At the time of imaging, an object placed on the top of a bed device is inserted into the opening portion.

A high voltage generator 109 applies a tube voltage (high voltage) between the cathode and anode of the X-ray tube 101. A filament current is supplied from the high voltage generator 109 to the filament of the X-ray tube 101. Upon receiving the tube voltage and the filament current, the target of the anode of the X-ray tube 101 emits X-rays.

The X-ray detector 103 includes a plurality of X-ray detection elements each having, for example, a 0.5 mm×0.5 mm square light-receiving surface. For example, 916 X-ray detection elements are arrayed in the channel direction (approximate to the Y-axis). For example, 64 arrays of the X-ray detection elements are arranged side by side in the slice direction (Z-axis).

A data acquisition system 104 generally called a DAS converts a signal output from the X-ray detector 103 for each channel into a voltage signal, amplifies it, and further converts it into a digital signal. This data (also called pure raw data) is supplied to a computer main body outside the gantry. A preprocessing device 106 of the computer main body performs preprocessing such as sensitivity correction for the pure raw data output from the data acquisition system 104. The preprocessed pure raw data is called raw data or projection data. Such data will be uniformly termed projection data hereinafter. A data storage device 112 stores projection data in association with each code representing a view number, channel number, and column number representing the position of the X-ray tube 101 at the time of data sampling.

Figure 3:
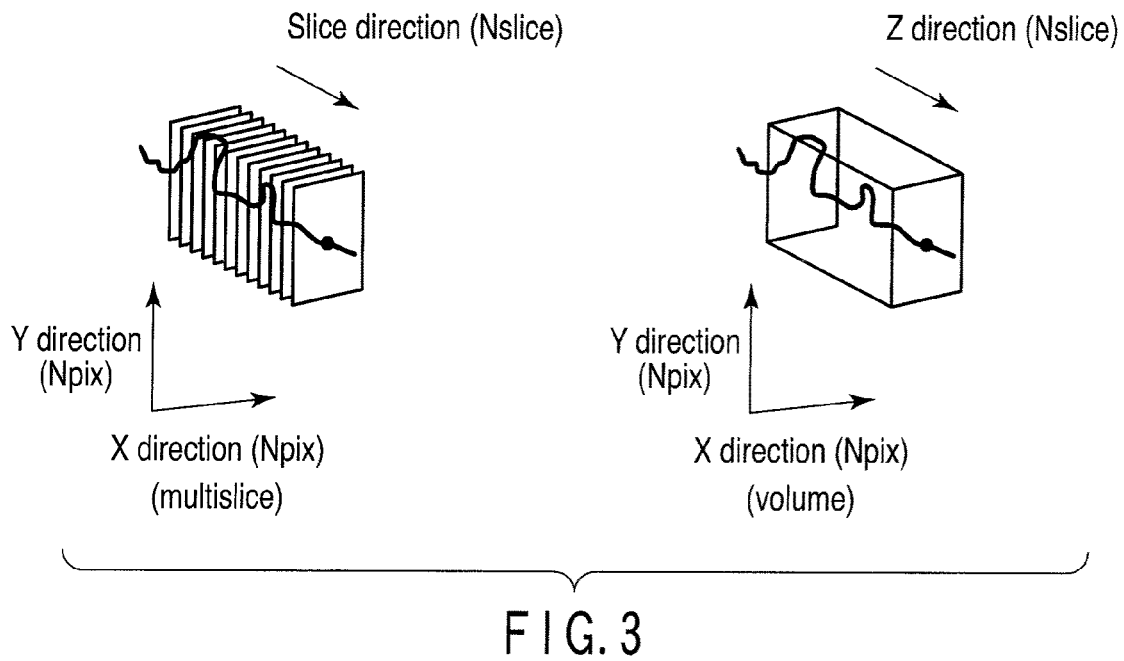
FIG. 3 is a view showing an example of a profile generated by a profile generating unit in FIG. 1.

The computer main body includes, in addition to the preprocessing device 106 and the data storage device 112, a scan controller 110, a reconstruction processing unit 114, a profile generating unit 201, a sector extraction unit 203, a scattered radiation distribution estimation unit 205, a scattered radiation correction profile generating unit 207, and a scattered radiation correction unit 209. The reconstruction processing unit 114 reconstructs multislice or volume image data by the Feldkamp reconstruction method based on the projection data detected by the X-ray detector 103. The data storage device 112 stores the image data. As shown in FIG. 3, multislice data is a group of a plurality of slice images (tomograms), and each pixel position is defined by X- and Y-coordinates and a slice number. Each pixel position of volume data is defined by X-, Y-, and Z-coordinates. In general, volume data is higher in resolution in the slice direction than multislice data. Three-dimensional data includes multislice data and volume data. Note that three-dimensional data will be described as multislice data.

Note that the data storage device 112 constitutes an image processing apparatus, together with the profile generating unit 201, sector extraction unit 203, scattered radiation distribution estimation unit 205, scattered radiation correction profile generating unit 207, and scattered radiation correction unit 209. Each unit of the image processing apparatus will be described below along with the following processing procedure.

FIG. 2 shows a scattered radiation correction processing procedure according to this embodiment. Note that the concept of this processing is to estimate a scattered radiation component from a profile in the slice direction which is generated from three-dimensional data for each pixel, correct the original profile in the slice direction by subtracting the scattered radiation component from the original profile in the slice direction, and obtain three-dimensional data having undergone scattered radiation correction by repeating these processes for all pixels.

A display device (not shown) reads additional information such as the imaging dates of all image data, patient names, and examination codes stored in the data storage device 112, and displays a list of the information (S11). A desired image is specified via an input device (not shown). The profile generating unit 201 receives the specified image data from the data storage device 112 (S12).

The profile generating unit 201 reduces the matrix size of image data of all the slices (to be referred to as original image data) (S13). That is, the profile generating unit 201 generates reduced original image data by decreasing the resolution of the original image data. If original image data has a matrix represented by Npix*Npix*Nslice, reduced image data has a matrix represented by (Npix/Nreduce_x)*(Npix/Nreduce_y)*(Nslice/Nreduce_z). Nreduce_x, Nreduce_y, and Nreduce_z each have a value of 1 or more. Note that matrix size reduction processing is the processing of making correction processing common to neighboring pixels and is merely supplementary processing for reducing the number of processing steps, which is not essential to scattered radiation correction.

Figure 4:
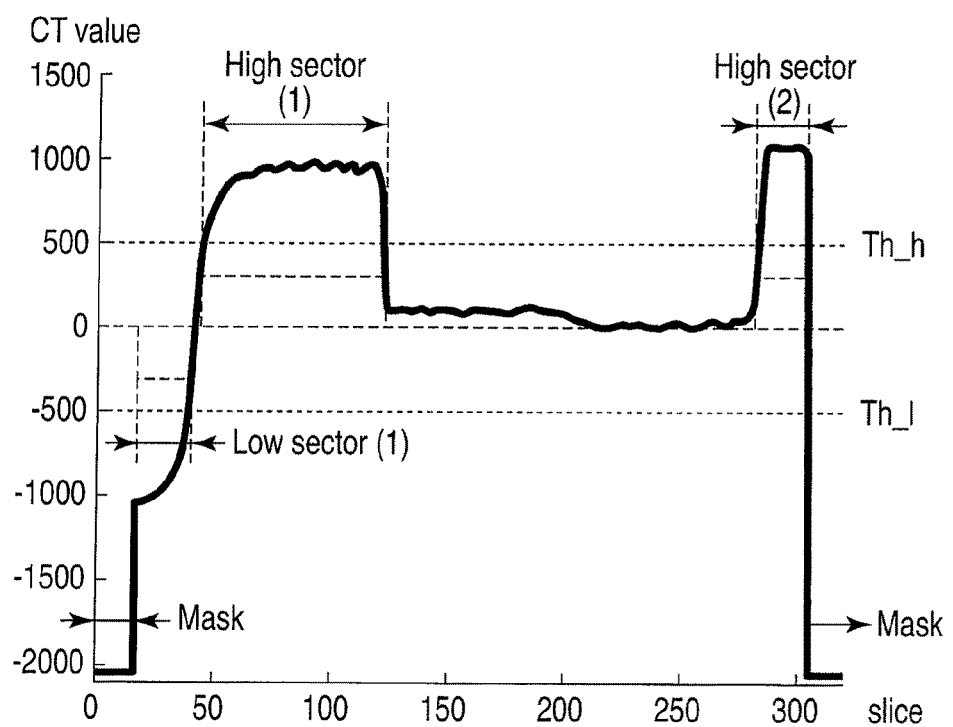
FIG. 4 is a graph showing an example of a sector extracted by a sector extraction unit in FIG. 1.

As shown in FIG. 3, the profile generating unit 201 generates a CT value profile representing a change in CT value in the slice direction (Z-axis direction) for each XY pixel of reduced image data (S14). A CT value profile is expanded with a slice number (a Z-axis when the volume form is used) when the ordinate and the abscissa respectively represent a CT value and a multislice. This profile represents changes in CT value in the slice direction. FIG. 4 shows an example of the CT value profile of a given pixel.

The sector extraction unit 203 extracts a sector from each CT value profile (S15). A sector represents a range in which the CT values are outstandingly higher or lower than those of the surroundings, i.e., a range in which the X-ray attenuation ratios are higher or lower. In other words, this range is a range in which scattered radiation tends to affect peripheral regions. This sector includes a high sector and a low sector, as shown in FIG. 4. A high sector is a range in which the CT values are higher than a first threshold Th-h. A low sector is a range in which the CT values are lower than a second threshold Th-l. If a plurality of high sectors consecutively appear, they can be regarded as one high sector. If a plurality of low sectors consecutively appear, they can be regarded as one low sector. In this case, a mask region is not a target for low sector extraction.

The scattered radiation distribution estimation unit 205 then estimates a positive scattered radiation distribution and a negative scattered radiation distribution which substantially represent changes in the occurrence frequency of scattered radiation in accordance with high and lower sectors, for each sector, as represented by equation (1) based on parameters provided in advance (S16).

$$Scat(\text{sector}[n])) = \text{power} * \frac{1}{\sqrt{2\pi}\,\sigma} e^{-\frac{(x-m)^2}{2\sigma^2}}$$

where $m = CenterSlice(\text{sector}[n])$ $\text{power} = \text{gscale\_a} * \sum_{slice=0}^{N(sector[n])} (CTvalue(\text{slice}) - Th\_base)$ $\sigma^2 = \text{gscale\_b} * N(\text{sector}[n])$ example of scattered radiation component derivation formula when scattered radiation distribution is Gaussian distribution, Scat(sector[n]): scattered radiation distribution (Gaussian distribution in this case) of sector [n], m: central slice of sector, power: scaling value of scattered radiation distribution (integral value of CT value differences from reference value is calculated and scaled with Gscale_a), Gscale_a: parameter which is changed in accordance with scan conditions/reconstruction conditions, σ: standard deviation of scattered radiation distribution, which is scaled with Gscale_b relative to sector length N(sector[n]), Gscale_b: parameter which is changed in accordance with scan conditions/reconstruction conditions, and Th_base: reference CT value for scattered radiation component calculation.

As a scattered radiation distribution, a Gaussian distribution is typically used, as shown in FIG. 5. The spread of a Gaussian distribution is determined by the width of a sector, and the height of the Gaussian distribution is determined by the integral value of CT values in the sector. The center of a scattered radiation distribution estimated by a Gaussian distribution is matched with the central position of the sector.

The scattered radiation correction profile generating unit 207 then generates a scattered radiation correction profile from the estimated scattered radiation distribution (S17). First of all, as shown in FIG. 6, the obtained scattered radiation distribution is weighted. A typical example of weighting is to assign 0 to the slices within the sector range and 1 to the remaining slices. The CT values themselves in the sector range are high, and hence the SNR is high. That is, the influence of scattered radiation is relatively low. In contrast, the influence of scattered radiation in the surroundings is high. Therefore, the above weights are effective. Obviously, changes in weight are not limited to the pattern in which 0 is assigned to the slices within the sector range and 1 to the remaining slices. For example, another pattern that can be used is the pattern in which 0 is assigned to the slices within the sector range, 0.5 is assigned to the slices within a predetermined range around the sector range, and 1 is assigned to the slices outside the range, or the pattern in which 0 is assigned to the slices within the sector range, and the weight to be assigned to the surrounding slices exponentially changes up to 1 with the distance to the sector range.

A correction profile for scattered radiation correction exemplified in FIG. 7 is generated by convoluting a plurality of weighted scattered radiation distributions.

The processing from the CT value profile generation processing in step S14 to the scattered radiation correction profile generation processing in step S17 is repeated for all the pixels (S18). The scattered radiation correction profile generating unit 207 then smoothes the scattered radiation correction profile in the slice direction, and further in the X-Y plane direction as needed (S19), and also restores (enlarges) it into the original matrix (Npix*Npix*Nslice) (S20). The enlargement method can use either one-dimensional interpolation, multi-dimensional interpolation, or duplication.

The scattered radiation correction unit 209 subtracts the scattered radiation correction profile generated in this manner from the original CT value profile of the original image data (S21).

Figure 8:
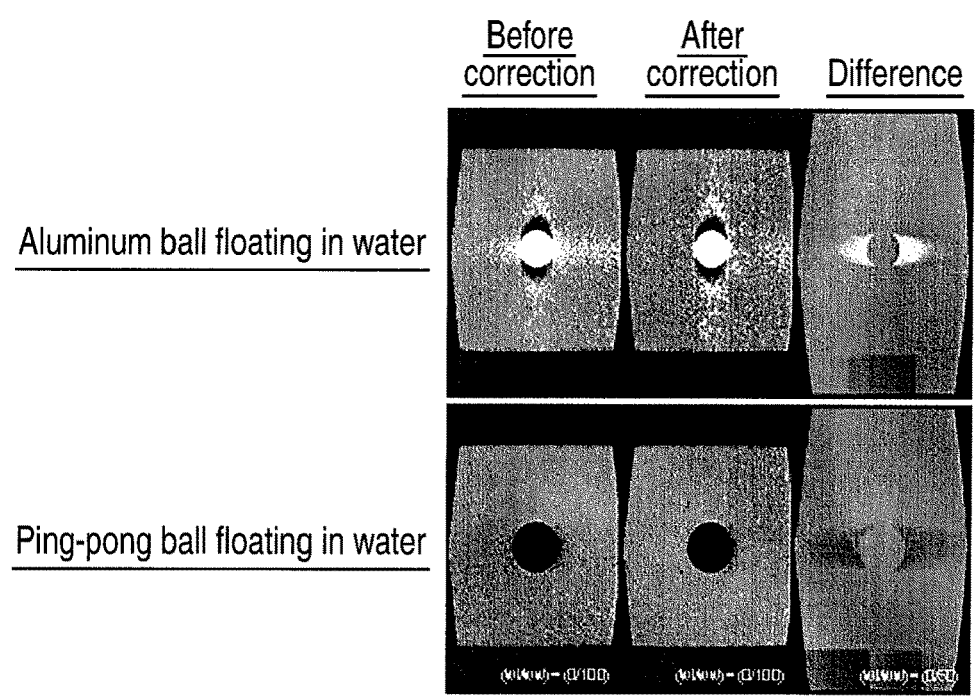
FIG. 8 is a view showing an example of an image corrected by a scattered radiation correction unit in FIG. 1.

This embodiment need not acquire any data for scattered radiation correction. The embodiment acquires image data and implements scattered radiation correction from the image data. FIG. 8 shows an example of a corrected image. Obviously, the scattered radiation is reduced, and the contour of the region is clarified.

This embodiment can be modified as follows.

(Scattered Radiation Correction for Volume Image Data Using Deconvolution Method)

An approximate curve used for the estimation of a scattered radiation distribution is not limited to a Gaussian distribution. It is possible to use a PSF (Point Spread Function). Letting h(y, z) be a PSF (Point Spread Function) representing the input/output characteristic of the influence of scattered radiation, g(y, z) be a multiplanar reformation image (MPR image) influenced by scattered radiation, f(x, y) be a true MPR image without the influence of scattered radiation, and H(u, v), G(u, v), and F(u, v) be Fourier transforms for the respective data, the following relational expressions hold:

$g(x,y)=h(y,z)*f(y,z)$ $G(u,v)=H(u,v)F(u,v)$ $G(u,v)=\zeta[g(y,z)]$ $H(u,v)=\zeta[h(y,z)]$ $F(u,v)=\zeta[f(y,z)]$ where ζ[ ] represents a Fourier transform.

Based on h(y, z) or H(u, v) defined in advance, f(y, z) is estimated from an MPR image g(y, z) influenced by scattered radiation (deconvolution method). It is possible to perform deconvolution processing once or a plurality of number of times and also to change h(y, z) for each convolution processing. For example, it is possible to use h(y, z) representing scattering by water for the first processing and h(y, z) representing scattering by a bone for the second processing. There is no need to limit a processing target to a (y, z) plane. A processing target can be a (x, z) or (x, y) plane or a one-dimensional plane.

(Generation of Scattered Radiation Correction Profile Targeted at All Pixels)

As shown in FIG. 9, it is possible to exclude matrix size reduction processing for original image data (S13) and scattered radiation correction profile enlargement processing (S18) and to generate a CT value profile for every XY pixel as a pixel of interest (S14), extract a sector (S15), estimate a scattered radiation distribution (S16), and generate a scattered radiation correction profile (S17).

(Scattered Radiation Correction for Volume Image Data Using Iterative Calculation)

Figure 10:
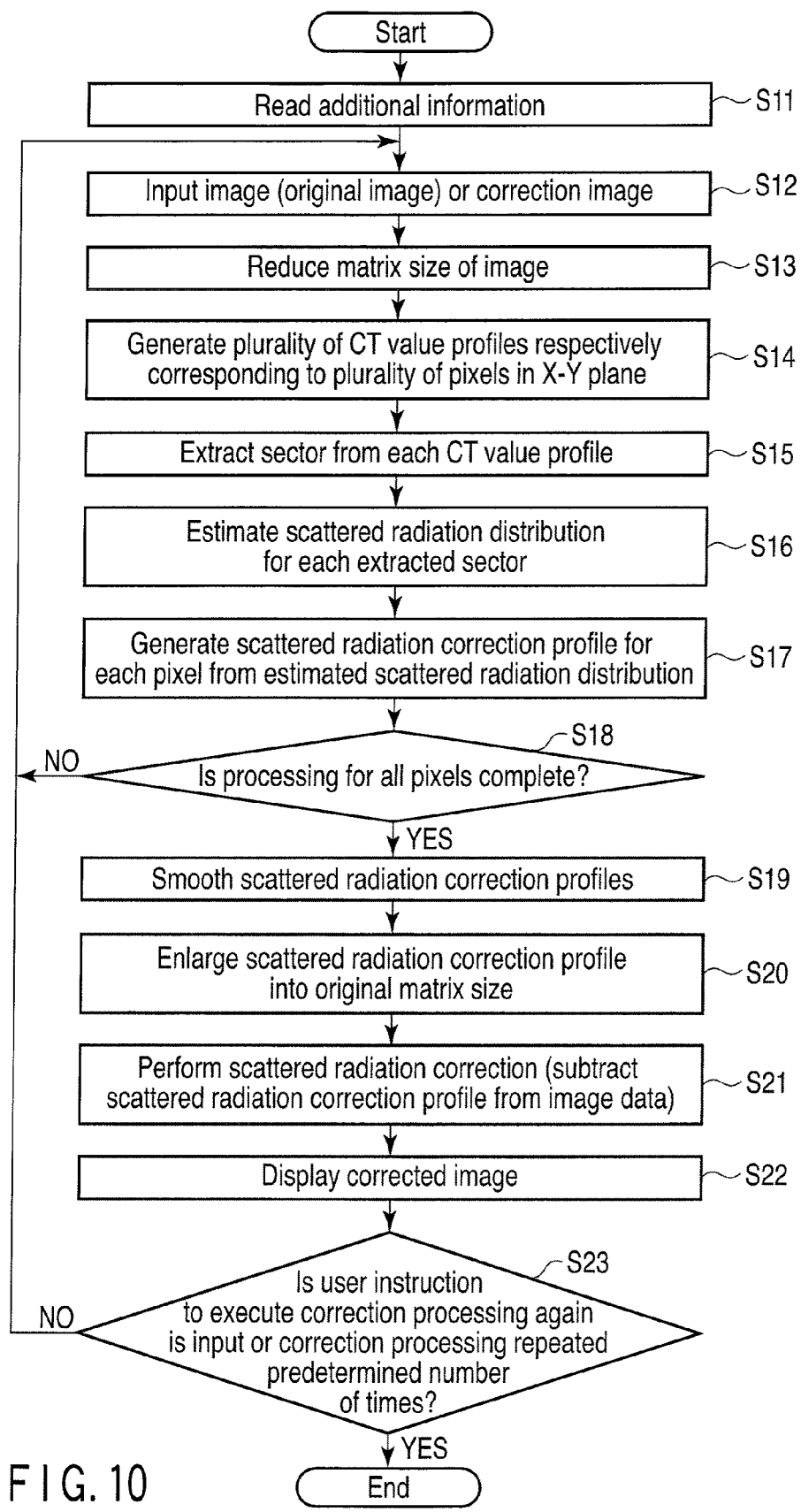
FIG. 10 is a flowchart showing still another scattered radiation correction processing procedure according to this embodiment.

As shown in FIG. 10, the scattered radiation correction processing shown in FIG. 2 can be repeated. Although the influence of scattered radiation appears as a low-frequency component on an MPR image, it is possible to use iterative calculation to suppress the low-frequency component. The image data having undergone scattered radiation correction is displayed (S22). The user checks a correction effect by seeing the displayed image. Upon determining that the correction is insufficient, the user inputs a correction instruction again. In accordance with the instruction, steps S12 to S21 are repeated for the image data having undergone scattered radiation correction as original image data. Note that the number of iterations may be set in advance.

(Extraction of Scattered Radiation Correction Target Pixel)

Figure 11:
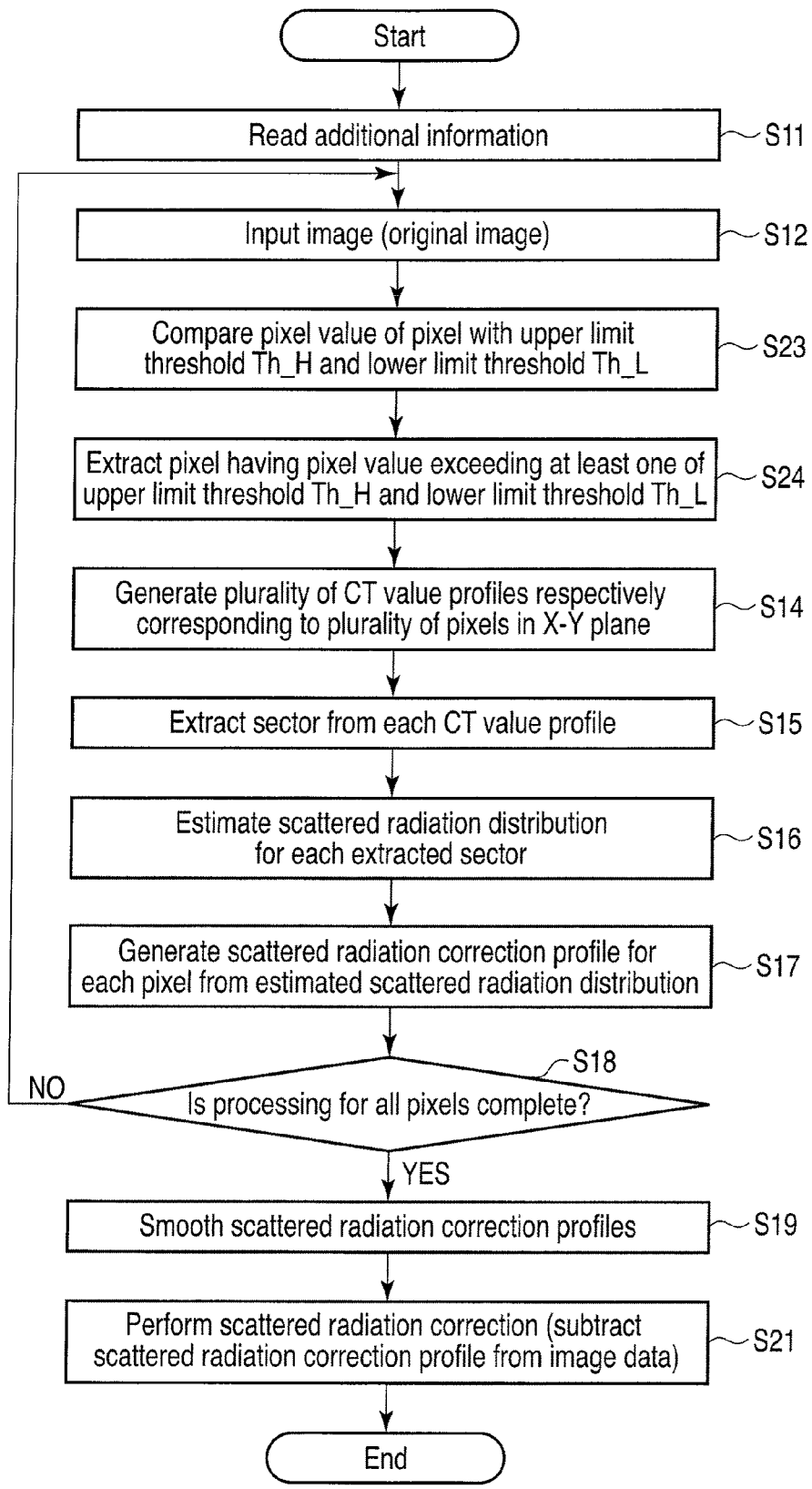
FIG. 11 is a flowchart showing still another scattered radiation correction processing procedure according to this embodiment.

As shown in FIG. 11, it is possible to extract a pixel for which scattered radiation correction is required and apply scattered radiation correction to only the extracted pixel instead of applying scattered radiation correction to all pixels. This processing eliminates the necessity of matrix size reduction processing for original image data. The CT values of all the pixels of all the slices of the original image data are compared with an upper limit threshold Th-H. Likewise, the CT values of all the pixels of all the slices of the original image data are compared with a lower limit threshold Th-L. The upper limit threshold Th-H is typically equivalent to the first threshold Th-h. However, a processing amount reduction effect is achieved when the upper limit threshold Th-H is higher than the first threshold Th-h or the lower limit threshold Th-L is lower than the second threshold Th-l. A pixel having a CT value higher than the upper limit threshold Th-H in at least one slice undergoes, as a scattered radiation correction target, the processing in steps S14 to S21. A pixel having a CT value lower than the lower limit threshold Th-L in at least one slice undergoes, as a scattered radiation correction target, the processing in steps S14 to S21.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computer tomography apparatus comprising:
   an X-ray tube which generates X-rays;
   an X-ray detector which detects X-rays transmitted through an object;
   a rotating mechanism which continuously rotates the X-ray tube and the X-ray detector around the object;
   a reconstruction unit which reconstructs one of multislice image data and volume image data based on projection data detected by the X-ray detector;
   a profile generating unit which generates a plurality of CT value profiles in a slice direction which respectively correspond to a plurality of pixels in a slice by using the image data;
   a profile portion extraction unit which extracts a profile portion exceeding a predetermined threshold from each of the CT value profiles;
   a scattered radiation distribution estimation unit which estimates a scattered radiation distribution centered on the profile portion, based on a CT value integral and width of the profile portion; and
   a scattered radiation correction unit which corrects the image data based on the estimated scattered radiation distribution.

2. The apparatus according to claim 1, wherein the scattered radiation correction unit includes
   a scattered radiation correction profile generating unit which generates a scattered radiation correction profile from the estimated scattered radiation distribution, and
   a subtraction unit which subtracts the scattered radiation correction profile from the CT value profile.

3. The apparatus according to claim 2, further comprising
   a reduction unit which reduces a matrix size of the image data, the CT value profile being generated from the reduced image data, and
   an enlargement unit which enlarges the scattered radiation correction profile into an original matrix size, the enlarged scattered radiation correction profile being subtracted from the CT value profile.

4. The apparatus according to claim 2, wherein the scattered radiation correction profile generating unit replaces a value within a range of the profile portion on the estimated scattered radiation distribution with a zero value.

5. The apparatus according to claim 1, wherein the profile portion extraction unit extracts another profile portion from each CT value profile by using another threshold.

6. The apparatus according to claim 1, wherein the scattered radiation distribution is approximated by a Gaussian distribution.

7. The apparatus according to claim 1, wherein the scattered radiation distribution is approximated by a point spread function.

8. The apparatus according to claim 1, wherein CT value profile generation processing by the profile generating unit, profile portion extraction processing by the profile portion extraction unit, scattered radiation distribution estimation processing by the scattered radiation distribution estimation unit, and correction processing for the CT value profile by the scattered radiation correction unit are repeated in accordance with one of a user instruction and a predetermined number of iterations.

9. The apparatus according to claim 1, further comprising a correction pixel extraction unit which extracts a pixel as a scattered radiation correction target by comparing a pixel value of the image data with another threshold.

10. An image processing apparatus comprising:
    a storage unit which stores one of multislice image data and volume image data concerning an object;
    a profile generating unit which generates a plurality of pixel value profiles in a slice direction which respectively correspond to a plurality of pixels in a slice by using the image data;
    a profile portion extraction unit which extracts a profile portion exceeding a predetermined threshold from each of the pixel value profiles;
    a scattered radiation distribution estimation unit which estimates a scattered radiation distribution centered on the profile portion based on a pixel value integral and width of the profile portion; and
    a scattered radiation correction unit which corrects the pixel value profile for each pixel based on the estimated scattered radiation distribution.

* * * * *